US008940661B2

(12) United States Patent
Mann et al.

(10) Patent No.: US 8,940,661 B2
(45) Date of Patent: Jan. 27, 2015

(54) SYNERGISTIC HERBICIDAL COMPOSITION CONTAINING FLUROXYPYR AND PENOXSULAM, HALOSULFURON-METHYL, IMAZAMOX OR IMAZETHAPYR

(71) Applicant: Dow AgroSciences LLC, Indianapolis, IN (US)

(72) Inventors: Richard K. Mann, Franklin, IN (US); Monte R. Weimer, Pittsboro, IN (US); Andrea Christine McVeigh-Nelson, Indianapolis, IN (US); Andrew Todd Ellis, Greenville, MS (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/079,468

(22) Filed: Nov. 13, 2013

(65) Prior Publication Data

US 2014/0066306 A1    Mar. 6, 2014

Related U.S. Application Data

(62) Division of application No. 13/678,451, filed on Nov. 15, 2012, now Pat. No. 8,614,167, which is a division of application No. 12/913,092, filed on Oct. 27, 2010, now Pat. No. 8,338,335.

(60) Provisional application No. 61/255,689, filed on Oct. 28, 2009.

(51) Int. Cl.
*A01N 43/40* (2006.01)
*A01N 43/54* (2006.01)
*A01N 43/50* (2006.01)
*A01N 43/90* (2006.01)

(52) U.S. Cl.
CPC ............... *A01N 43/40* (2013.01); *A01N 43/54* (2013.01); *A01N 43/50* (2013.01); *A01N 43/90* (2013.01)
USPC ......................................................... 504/130

(58) Field of Classification Search
CPC .................................................... A01N 43/40
See application file for complete search history.

(56) References Cited

U.S. PATENT DOCUMENTS

| 5,236,887 | A | 8/1993 | Noveroske |
| 5,858,924 | A | 1/1999 | Johnson et al. |
| 5,990,047 | A | 11/1999 | Hacker et al. |
| 2011/0098181 | A1 | 4/2011 | Mann et al. |
| 2012/0108428 | A1 | 5/2012 | Mann et al. |

FOREIGN PATENT DOCUMENTS

| CN | 101 066 056 A | 11/2007 |
| CN | 101 433 205 A | 5/2009 |
| CN | 101 530 103 A | 9/2009 |
| CN | 101 530 104 A | 9/2009 |
| CN | 101 530 105 A | 9/2009 |
| CN | 101 669 482 A | 3/2010 |
| EP | 0 512 739 A1 | 11/1992 |
| WO | WO 2008/058622 A2 | 5/2008 |
| WO | WO 2009/152827 A2 | 12/2009 |

OTHER PUBLICATIONS

Disclosed Anonymously 462055: "2-(2,2-difluoroethoxy)-6-triftuoromethyl-N-(5,8-dimethoxy[1,2,4]triazolo[1,5-c]pyrimidin-2-yl)benzenesulfonamide and its use as a herbicide in mixtures," Research Disclosure, Oct. 2002, pp. 1832-1833.
"Penoxsulam and its use as a herbicide in mixtures for use in rice, wheat, barely, oats, sorghum, corn, maize, lvm, rangeland pastures, grasslands, fallowland, turf, and aquatics" The IP.com Journal, vol. 5, No. 4, Apr. 2005, pp. 286-293.
Database WPI, Section Ch, Week 200969, "Herbicide composition for preventing graminaceous and broadleaved weed D in rice field comprises active ingredients including sulfonylurea or its salt, pyridines and penoxsulam at specified weight ratio," Thomson Scientific, London, GB; Class A97, An 2009-N99318. Beijing Yingtaijiahe Science, Sep. 16, 2009.
Anonymous: "Clearmax herbicide Label," BASF Corporation (2008).
Brown et al., "Safening grain sorghum injury from metsulfuron with growth regulator herbicides," Weed Sci. 52:319-325 (2004).
Lym et al., "Leafy spurge control with various picolinic acid herbicides," Leafy Spurge Symposium, Riverton, WY pp. 78-79 (1986).
Nelson et al., "Imazapyr and Triclopyr Tank Mixtures for Basal Bark Control of Woody Brush in the Southeastern United States," *New Forests* 31(2):173-183 (2006).
Nespeca, Mathew C., "Interactive Effects of Imazapyr plus Triclopyr ester and Imazapyr plus Glyphosate Mixtures on Woody Weed Seedlings—abstract," Thesis submitted to the Faculty of Virginia Polytechnic Institute and State University in partial fulfillment of the requirements for the degree of Master of Science in Forestry, Blacksburg, VA (1997).
Pellerin et al., "Potential use of imazethapyr mixtures in drill-seeded imidazolinone-resistant rice," *Weed Technol.* 18(4):1037-1042 (2004).
Pellerin, Kristie J., "Management of Imidazolinone Tolerant (IT) Rice in Drill- and Waterseeded Rice, Thesis submitted to the Graduate Faculty of the Louisiana State University and Agricultural and Mechanical College in partial fulfillment of the requirements for the degree of Master of Science in the Department of Plant Pathology and Crop Physiology.", 2002.
Weimer et al., "Performance of Cereal Grass Herbicides in Tank-Mix Combinations with Fluroxypyr, Clopyralid, Aminopyralid, Bromoxynil, and MCPA Mixtures," North Central Weed Science Society Proceedings 61:105 (2006).

*Primary Examiner* — Alton Pryor
(74) *Attorney, Agent, or Firm* — Michael R. Asam

(57) ABSTRACT

An herbicidal synergistic composition containing (a) fluroxypyr and (b) an ALS inhibitor herbicide, in which the ALS inhibitor herbicide is penoxsulam, halosulfuron-methyl, imazamox or imazethapyr, provides improved post-emergence weed control in rice, cereal and grain crops, pastures, rangelands, IVM and turf.

19 Claims, No Drawings

SYNERGISTIC HERBICIDAL COMPOSITION CONTAINING FLUROXYPYR AND PENOXSULAM, HALOSULFURON-METHYL, IMAZAMOX OR IMAZETHAPYR

FIELD OF THE INVENTION

This application is a divisional of U.S. application Ser. No. 13/678,451, filed Nov. 15, 2012, now allowed, which is a divisional of U.S. application Ser. No. 12/913,092, filed Oct. 27, 2010, now U.S. Pat. No. 8,338,335, which claims the benefit of U.S. Provisional Application Ser. No. 61/255,689, filed Oct. 28, 2009, the entireties of which are incorporated herein by reference.

This invention concerns a synergistic herbicidal composition containing (a) fluroxypyr and (b) at least one herbicide selected from the group consisting of penoxsulam, halosulfuron-methyl, imazamox and imazethapyr for controlling weeds in crops, especially rice, cereal and grain crops, pastures, rangelands, industrial vegetation management (IVM) and turf. These compositions provide improved post-emergence herbicidal weed control.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Eighth Edition, 2002, p. 462 "'synergism' [is] an interaction of two or more factors such that the effect when combined is greater than the predicted effect based on the response to each factor applied separately." The present invention is based on the discovery that fluroxypyr, penoxsulam, halosulfuron-methyl and imazamox, already known individually for their herbicidal efficacy, display a synergistic effect when applied in combination.

The herbicidal compounds forming the synergistic composition of this invention are independently known in the art for their effects on plant growth.

SUMMARY OF THE INVENTION

The present invention concerns a synergistic herbicidal mixture comprising an herbicidally effective amount of (a) fluroxypyr and (b) an acetolactate synthase (ALS) inhibitor herbicide. ALS inhibitor herbicides include compounds from the classes of sulfonamides, sulfonylureas and imidazolinones. Particularly useful ALS inhibitor herbicides include, but are not limited to, penoxsulam, halosulfuron-methyl, imazamox and imazethapyr. The compositions may also contain an agriculturally acceptable adjuvant and/or carrier.

The present invention also concerns herbicidal compositions for and methods of controlling the growth of undesirable vegetation, particularly in monocot crops including rice, wheat, barley, oats, rye, sorghum, corn, maize, pastures, grasslands, rangelands, fallowland, turf, IVM and aquatics and the use of these synergistic compositions.

The species spectra of ALS inhibitors like penoxsulam, halosulfuron-methyl, imazamox and imazethapyr, i.e., the weed species which the respective compounds control, are broad and highly complementary with that of fluroxypyr. For example, it has been surprisingly found that a combination of penoxsulam and fluroxypyr exhibits a synergistic action in the control of Hemp sesbania (*Sesbania exaltata*; SEBEX), Texasweed (*Caperonia palustris*; CNPPA), Japanese bulrush (*Scirpus juncoides*; SCPJU), narrow-leaved plantain (*Plantago lanceolata* L.; PLALA), and barnyardgrass (*Echinochloa crus-galli*; ECHCG) at application rates equal to or lower than the rates of the individual compounds. Similarly, it has been surprisingly found that a combination of halosulfuron-methyl and fluroxypyr exhibits a synergistic action in the control of barnyardgrass (*Echinochloa crus-galli*; ECHCG), Chinese sprangletop (*Leptochloa chinensis*; LEFCH), and yellow nutsedge (*Cyperus esculentus*; CYPES) at application rates equal to or lower than the rates of the individual compounds. In addition, it has been surprisingly found that a combination of imazamox and fluroxypyr exhibits a synergistic action in the control of barnyardgrass (*Echinochloa crus-galli*; ECHCG), broadleaf signalgrass (*Brachiaria platyphylla*; BRAPP), and yellow nutsedge (*Cyperus esculentus*; CYPES) at application rates equal to or lower than the rates of the individual compounds. In addition, it has been surprisingly found that a combination of imazethapyr and fluroxypyr exhibits a synergistic action in the control of sprangletop grass (*Leptochloa* spp, LEFSS) and fall *panicum* (*Panicum dichotomiflorum*, PANDI) at application rates equal to or lower than the rates of the individual compounds.

DETAILED DESCRIPTION OF THE INVENTION

Fluroxypyr is the common name for [(4-amino-3,5-dichloro-6-fluoro-2-pyridinyl)oxy]acetic acid. Its herbicidal activity is described in *The Pesticide Manual*, Fourteenth Edition, 2006. Fluroxypyr controls a wide range of economically important broadleaf weeds. It can be used as the acid itself or as an agriculturally acceptable salt or ester. Use as an ester is preferred, with the meptyl ester being most preferred.

Penoxsulam is the common name for 2-(2,2-difluoroethoxy)-N-(5,8-dimethoxy-[1,2,4]triazolo[1,5-c]pyrimidin-2-yl)-6-(trifluoromethyObenzenesulfonamide. Its herbicidal activity is described in *The Pesticide Manual*, Fourteenth Edition, 2006. Penoxsulam controls *Echinochloa* spp., as well as many broadleaf, sedge and aquatic weeds in rice, and *Apera* spp. in grass, as well as many broadleaf weeds in cereals.

Halosulfuron-methyl is the common name for methyl 3-chloro-5-[[[[(4,6-dimethoxy-2-pyrimidinyl)amino]carbonyl]amino]sulfonyl]-1-methyl-1H-pyrazole-4-carboxylate. Its herbicidal activity is described in *The Pesticide Manual*, Fourteenth Edition, 2006. Halosulfuron-methyl controls many broadleaf and nutsedge weeds in rice, corn, sorghum, sugar cane, nuts and turf.

Imazamox is the common name for 2-[4,5-dihydro-4-methyl-4-(1-methylethyl)-5-oxo-1H-imidazol-2-yl]-5-(methoxymethyl)-3-pyridinecarboxylic acid. Its herbicidal activity is described in *The Pesticide Manual*, Fourteenth Edition, 2006. Imazamox controls many broadleaf weeds in corn, rape, alfalfa, peas and beans.

Imazethapyr is the common name for 2-[4,5-dihydro-4-methyl-4-(1-methylethyl)-5-oxo-1H-imidazol-2-yl]-5-ethyl-3-pyridinecarboxylic acid. Its herbicidal activity is described in *The Pesticide Manual*, Fourteenth Edition, 2006.

Imazethapyr controls many grass and broadleaf weeds in alfalfa, peas, beans, soybeans and imidazolinone tolerant rice and corn.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

In the composition of this invention, the weight ratio of fluroxypyr (acid equivalent) to ALS inhibitor herbicide (active ingredient) at which the herbicidal effect is synergistic lies within the range of between about 1:2 and about 140:1.

The rate at which the synergistic composition is applied will depend upon the particular type of weed to be controlled, the degree of control required, and the timing and method of application. The ALS inhibitor herbicide is applied at a rate between about 4 g ai/ha and about 100 g ai/ha and fluroxypyr is applied at a rate between about 50 g ae/ha and about 560 g ae/ha.

The components of the synergistic mixture of the present invention can be applied either separately or as part of a multipart herbicidal system, which can be provided as a premix or a tank mix.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: 2,4-D, acetochlor, acifluorfen, aclonifen, AE0172747, alachlor, amidosulfuron, aminotriazole, ammonium thiocyanate, anilifos, atrazine, AVH 301, azimsulfuron, benfuresate, bensulfuron-methyl, bentazone, benthiocarb, benzobicyclon, bifenox, bispyribac-sodium, bromacil, bromoxynil, butachlor, butafenacil, butralin, cafenstrole, carbetamide, carfentrazone-ethyl, chlorflurenol, chlorimuron, chlorpropham, cinosulfuron, clethodim, clomazone, clopyralid, cloransulam-methyl, cyclosulfamuron, cycloxydim, cyhalofop-butyl, dicamba, dichlobenil, dichlorprop-P, diclosulam, diflufenican, diflufenzopyr, dimethenamid, dimethenamid-p, diquat, dithiopyr, diuron, EK2612, EPTC, esprocarb, ET-751, ethoxysulfuron, ethbenzanid, F7967, fenoxaprop, fenoxaprop-ethyl, fenoxaprop-ethyl+isoxadifen-ethyl, fentrazamide, flazasulfuron, florasulam, fluazifop, fluazifop-P-butyl, flucetosulfuron (LGC-42153), flufenacet, flufenpyr-ethyl, flumetsulam, flumiclorac-pentyl, flumioxazin, fluometuron, flupyrsulfuron, fomesafen, foramsulfuron, fumiclorac, glufosinate, glufosinate-ammonium, glyphosate, haloxyfop-methyl, haloxyfop-R, imazamethabenz, imazapic, imazapyr, imazaquin, imazosulfuron, indanofan, indaziflam, iodosulfuron, ioxynil, ipfencarbazone (HOK-201), IR 5790, isoproturon, isoxaben, isoxaflutole, KUH-071, lactofen, linuron, MCPA, MCPA ester & amine, mecoprop-P, mefenacet, mesosulfuron, mesotrione, metamifop, metazosulfuron (NC-620), metolachlor, metosulam, metribuzin, metsulfuron, molinate, MSMA, napropamide, nicosulfuron, norflurazon, OK-9701, orthosulfamuron, oryzalin, oxadiargyl, oxadiazon, oxazichlomefone, oxyfluorfen, paraquat, pendimethalin, pentoxazone, pethoxamid, picloram, picolinafen, piperophos, pretilachlor, primisulfuron, profoxydim, propachlor, propanil, propyrisulfuron (TH-547), propyzamide, prosulfocarb, prosulfuron, pyraclonil, pyrazogyl, pyrazosulfuron, pyribenzoxim (LGC-40863), pyriftalid, pyriminobac-methyl, pyrimisulfan (KUH-021), pyroxsulam, pyroxasulfone (KIH-485), quinclorac, quizalofop-ethyl-D, S-3252, sethoxydim, simazine, SL-0401, SL-0402, S-metolachlor, sulcotrione, sulfentrazone, sulfosate, tebuthiuron, tefuryltrione (AVH-301), terbacil, thiazopyr, thiobencarb, triclopyr, trifluralin and tritosulfuron.

The synergistic composition of the present invention can, further, be used in conjunction with glyphosate, glufosinate, dicamba, imidazolinones, sulfonylureas, or 2,4-D on glyphosate-tolerant, glufosinate-tolerant, dicamba-tolerant, imidazolinone-tolerant, sulfonylurea-tolerant and 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, 829148 and N-phenyl-sulfonylbenzoic acid amides, to enhance their selectivity. Cloquintocet (mexyl) is a particularly preferred safener for the synergistic compositions of the present invention, specifically antagonizing any harmful effect of the synergistic compositions on rice and cereals.

The synergistic mixture of fluroxypyr and penoxsulam of the present invention also provides a safening effect when applied to sunflower (*Helianthus annuus*; HELAN) and centipedegrass (*Eremochloa ophiuroides*; ERLOP). Another aspect of the present invention is a method for protecting centipedegrass and sunflower from the individual harmful effects of penoxsulam and fluroxypyr which comprises contacting centipedegrass or sunflower, or applying to the area under cultivation, a safening amount of a synergistic mixture of penoxsulam and fluroxypyr.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulators, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 0.01 to 90 percent by weight are often employed. In compositions designed to be employed as concentrates, the active ingredients are generally present in a concentration from 1 to 98 weight percent, preferably 5 to 90 weight percent. Such compositions are typically diluted with an inert carrier, such as water, before application, or applied as a dry or liquid formulation directly into flooded rice fields. The diluted compositions usually applied to weeds or the locus of weeds generally contain 0.0001 to 10 weight percent active ingredient and preferably contain 0.001 to 5.0 weight percent.

The present compositions can be applied to weeds or their locus by the use of conventional ground or aerial dusters, sprayers, and granule applicators, by addition to irrigation or paddy water, and by other conventional means known to those skilled in the art.

The following examples illustrate the present invention.

Evaluation of Postemergence Herbicidal Activity of Mixtures in the Greenhouse

Seeds of the desired test plant species were planted in 80% mineral soil/20% grit planting mixture, which typically has a pH of 7.2 and an organic matter content of about 2.9 percent, in plastic pots with a surface area of 128 square centimeters ($cm^2$). The growing medium was steam sterilized. The plants were grown for 7-19 days in a greenhouse with an approximate 14-hour (h) photoperiod which was maintained at about 29° C. during the day and 26° C. during the night. Nutrients and water were added on a regular basis and supplemental lighting was provided with overhead metal halide 1000-Watt lamps as necessary. The plants were treated with postemergence foliar applications when they reached the third to fourth true leaf stage. All treatments were applied using a randomized complete block trial design, with 4 replications per treatment.

Evaluation of Postemergence Herbicidal Activity of Mixtures in the Greenhouse

Treatments consisted of the compounds as listed in Tables 1, 3, 5 and 6, each compound applied alone and in combination. Formulated amounts of penoxsulam, halosulfuron-methyl, imazamox and fluroxypyr-meptyl ester, were placed in 60 milliliter (mL) glass vials and dissolved in a volume of 60 mL of a water solution containing Agri-dex crop oil concentrate in a 1% volume per volume (v/v) ratio. Compound requirements are based upon a 12 mL application volume at a rate of 187 liters per hectare (L/ha). Spray solutions of the mixtures were prepared by adding the stock solutions to the appropriate amount of dilution solution to form 12 mL spray solution with active ingredients in single and two way combinations. Formulated compounds were applied to the plant material with an overhead Mandel track sprayer equipped with 8002E nozzles calibrated to deliver 187 L/ha at a spray height of 18 inches (43 centimeters (cm)) above average plant canopy.

The treated plants and control plants were placed in a greenhouse as described above and watered by sub-irrigation to prevent wash-off of the test compounds. Treatments were rated at 7 to 21 days after application (DAA) as compared to the untreated control plants. Visual weed control was scored on a scale of 0 to 100 percent where 0 corresponds to no injury and 100 corresponds to complete kill.

Evaluation of Postemergence Herbicidal Activity of Mixtures in the Field

Field trials were conducted in rice and turf using standard herbicide small plot research methodology. Plots varied from 3×3 meter (m) to 3×10 m (width×length) with 4 replicates per treatment. The rice crop was grown using normal cultural practices for fertilization, seeding, watering, flooding and maintenance to ensure good growth of the crop and the weeds. The turf crop was a permanent established crop of centipedegrass that was grown and maintained under normal cultural practices for fertilization, watering, mowing and disease maintenance to ensure good growth of the crop and the weeds.

All treatments in the field trials were applied using a carbon dioxide ($CO_2$) backpack sprayer calibrated to apply 187 L/ha spray volume. Commercially available products of penoxsulam and fluroxypyr-meptyl were mixed in water at appropriately formulated product rates to achieve the desired rates based on a unit area of application (hectare) to achieve the desired rates as shown. Treatments were rated at 7 to 33 days after application as compared to the untreated control plants. Visual weed control was scored on a scale of 0 to 100 percent where 0 corresponds to no injury and 100 corresponds to complete kill.

Table 2 demonstrates the herbicidal synergistic efficacy of penoxsulam+fluroxypyr-meptyl tank mixes on weed control. Table 4 demonstrates the herbicidal synergistic safening of two crops to mixtures of penoxsulam+fluroxypyr-meptyl. Table 7 demonstrates the herbicidal synergistic efficacy of imazethapyr+fluroxypyr-meptyl tank mixes on weed control. All treatment results, both for the single product and mixtures, are an average of 3 to 4 replicates and the tank mix interactions are significant at the P>0.05 level.

Colby's equation was used to determine the herbicidal effects expected from the mixtures (Colby, S. R. Calculation of the synergistic and antagonistic response of herbicide combinations. *Weeds* 1967, 15, 20-22.).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Tables 1-7. All comparisons are an average of 3-4 replicates and are significant at the P>0.05 level. Rates of penoxsulam, halosulfuron-methyl, imazamox and imazethapyr are expressed in grams active ingredient/hectare (g ai/ha) and rates of fluroxypyr are expressed in grams acid equivalent (g ae)/hectare in Tables 1-7.

TABLE 1

Synergistic Activity of Herbicidal Compositions of Penoxsulam + Fluroxypyr-meptyl on grass weeds (*Echinochloa crus-galli* (ECHCG)) in the greenhouse.

| Application Rates | | % Control ECHCG | |
|---|---|---|---|
| Penoxsulam | Fluroxypyr-meptyl | | |
| (g ai/ha) | (g ae/ha) | Ob | Ex |
| 15 | 0 | 62 | — |
| 0 | 340 | 0 | — |
| 15 | 340 | 80 | 62 |
| 15 | 0 | 84 | — |
| 0 | 340 | 0 | — |
| 15 | 340 | 90 | 84 |
| 15 | 0 | 78 | — |
| 0 | 340 | 0 | — |
| 15 | 340 | 93 | 78 |

TABLE 2

Synergistic Activity of Herbicidal Compositions of Penoxsulam + Fluroxypyr-meptyl on broadleaf weeds (*Plantago lanceolata*, PLALA; *Caperonia palustris*, CNPPA; and Sebex exaltata, SEBEX) in the field.

| Application Rate | | % Control | | | | | |
|---|---|---|---|---|---|---|---|
| Penoxsulam | Fluroxypyr-meptyl | PLALA | | CNPPA | | SEBEX | |
| (g ai/ha) | (g ae/ha) | Ob | Ex | Ob | Ex | Ob | Ex |
| 15 | 0 | 13 | — | — | — | | |
| 0 | 140 | 0 | — | — | — | | |
| 15 | 140 | 83 | 13 | — | — | | |
| 35 | 0 | — | — | 67 | — | | |
| 0 | 97 | — | — | 45 | — | | |
| 35 | 97 | — | — | 93 | 82 | | |
| 35 | 0 | — | — | 67 | — | | |
| 0 | 290 | — | — | 60 | — | | |
| 35 | 290 | — | — | 97 | 87 | | |
| 22 | 0 | — | — | — | — | 76 | — |
| 0 | 97 | — | — | — | — | 57 | — |
| 22 | 97 | — | — | — | — | 100 | 90 |

TABLE 3

Synergistic Activity of Herbicidal Compositions of Penoxsulam + Fluroxypyr-meptyl on perennial rice weed *Scirpus juncoides* (SCPJU) in the greenhouse.

| Application Rate | | % Control SCPJU | |
|---|---|---|---|
| Penoxsulam | Fluroxypyr-meptyl | | |
| (g ai/ha) | (g ae/ha) | Ob | Ex |
| 10 | 0 | 2 | — |
| 0 | 70 | 60 | — |
| 10 | 70 | 66 | 60 |

TABLE 4

Synergistic Activity of Herbicidal Compositions of Penoxsulam + Fluroxypyr-meptyl on safening of injury in Sunflower (HELAN) and Centipedegrass (ERLOP) in the field.

| Application Rate | | % Injury | | | |
|---|---|---|---|---|---|
| Penoxsulam | Fluroxypyr-meptyl | HELAN | | ERLOP | |
| (g ai/ha) | (g ae/ha) | Ob | Ex | Ob | Ex |
| 7.5 | 0 | 36 | — | — | — |
| 0 | 100 | 31 | — | — | — |
| 7.5 | 100 | 36 | 56 | — | — |
| 15 | 0 | 40 | — | — | — |
| 0 | 100 | 34 | — | — | — |
| 15 | 100 | 50 | 60 | — | — |
| 30 | 0 | 41 | — | — | — |
| 0 | 100 | 34 | — | — | — |
| 30 | 100 | 46 | 61 | — | — |
| 70 | 0 | — | — | 15 | — |
| 0 | 210 | — | — | 6 | — |
| 70 | 210 | — | — | 13 | 24 |

TABLE 5

Synergistic Activity of Herbicidal Compositions of Halosulfuron-methyl + Fluroxypyr-meptyl on rice weeds in the greenhouse (rated 21 days after application (DAA)).

| Application Rate | | % Control | | | | | |
|---|---|---|---|---|---|---|---|
| Halosulfuron-methyl | Fluroxypyr-meptyl | ECHCG | | CYPES | | LEFCH | |
| (g ai/ha) | (g ae/ha) | Ob | Ex | Ob | Ex | Ob | Ex |
| 4.4 | 0 | — | — | 68 | — | — | — |
| 0 | 50 | — | — | 1 | — | — | — |
| 4.4 | 50 | — | — | 78 | 68 | — | — |
| 4.4 | 0 | — | — | 68 | — | — | — |
| 0 | 100 | — | — | 3 | — | — | — |
| 4.4 | 100 | — | — | 77 | 69 | — | — |
| 4.4 | 0 | — | — | 68 | — | 2 | — |
| 0 | 200 | — | — | 8 | — | 15 | — |
| 4.4 | 200 | — | — | 84 | 71 | 40 | 17 |
| 8.8 | 0 | 3 | — | 73 | — | — | — |
| 0 | 50 | 6 | — | 1 | — | — | — |
| 8.8 | 50 | 30 | 9 | 84 | 73 | — | — |
| 8.8 | 0 | 3 | — | — | — | — | — |
| 0 | 100 | 2 | — | — | — | — | — |
| 8.8 | 100 | 29 | 4 | — | — | — | — |
| 8.8 | 0 | 3 | — | 73 | — | — | — |
| 0 | 200 | 11 | — | 8 | — | — | — |
| 8.8 | 200 | 24 | 14 | 92 | 75 | — | — |
| 18 | 0 | 6 | — | 78 | — | — | — |
| 0 | 50 | 6 | — | 1 | — | — | — |
| 18 | 50 | 33 | 11 | 92 | 78 | — | — |
| 18 | 0 | 6 | — | — | — | — | — |
| 0 | 100 | 2 | — | — | — | — | — |
| 18 | 100 | 34 | 7 | — | — | — | — |
| 18 | 0 | 6 | — | 78 | — | 8 | — |
| 0 | 200 | 11 | — | 8 | — | 15 | — |
| 18 | 200 | 33 | 16 | 98 | 79 | 50 | 22 |

TABLE 6

Synergistic Activity of Herbicidal Compositions of Imazamox + Fluroxypyr-meptyl on rice weeds in the greenhouse (rated 21 days after application (DAA)).

| Application Rate | | % Control | | | | | |
|---|---|---|---|---|---|---|---|
| Imazamox | Fluroxypyr-meptyl | ECHCG | | BRAPP | | CYPES | |
| (g ai/ha) | (g ae/ha) | Ob | Ex | Ob | Ex | Ob | Ex |
| 4.4 | 0 | 1.3 | — | 3 | — | — | — |
| 0 | 50 | 1.3 | — | 10 | — | — | — |
| 4.4 | 50 | 32 | 2.4 | 55 | 12 | — | — |
| 4.4 | 0 | 1.3 | — | 3 | — | — | — |
| 0 | 100 | 4 | — | 23 | — | — | — |
| 4.4 | 100 | 66 | 5 | 50 | 25 | — | — |
| 4.4 | 0 | 1.3 | — | 3 | — | — | — |
| 0 | 200 | 6 | — | 20 | — | — | — |
| 4.4 | 200 | 84 | 7 | 60 | 21 | — | — |
| 8.8 | 0 | 29 | — | 46 | — | — | — |
| 0 | 50 | 1.3 | — | 10 | — | — | — |
| 8.8 | 50 | 100 | 30 | 76 | 52 | — | — |
| 8.8 | 0 | 29 | — | 46 | — | 8 | — |
| 0 | 100 | 4 | — | 23 | — | 10 | — |
| 8.8 | 100 | 100 | 31 | 86 | 58 | 39 | 17 |
| 8.8 | 0 | 29 | — | 46 | — | 8 | — |
| 0 | 200 | 6 | — | 20 | — | 9 | — |
| 8.8 | 200 | 100 | 33 | 92 | 57 | 33 | 16 |
| 18 | 0 | 85 | — | — | — | — | — |
| 0 | 50 | 1.3 | — | — | — | — | — |
| 18 | 50 | 100 | 85 | — | — | — | — |
| 18 | 0 | — | — | — | — | 42 | — |
| 0 | 200 | — | — | — | — | 9 | — |
| 18 | 200 | — | — | — | — | 57 | 47 |

TABLE 7

Synergistic Activity of Herbicidal Compositions of Imazethapyr + Fluroxypyr-meptyl on grass weeds (*Leptochloa* spp, LEFSS and *Panicum dichotomiflorum*, PANDI) in the field.
% Control

| Application Rate | | LEFSS | | PANDI | |
|---|---|---|---|---|---|
| Imazethapyr | Fluroxypyr-meptyl | Ob | Ex | Ob | Ex |
| (g ai/ha) | (g ae/ha) | | | | |
| 70 | 0 | 28 | — | 40 | — |
| 0 | 290 | 0 | — | 0 | — |
| 70 | 290 | 76 | 28 | 95 | 40 |

BRAPP=*Brachiaria platyphylla*; broadleaf signalgrass
CNPPA=*Caperonia palustris*; Texasweed
CYPES=*Cyperus esculentus*; yellow nutsedge
ECHCG=*Echinochloa crus-galli*; barnyardgrass
ERLOP,=*Eremochloa ophiuroide*; centipedegrass
HELAN=*Helianthus annuus*; sunflower
LEFCH=*Leptochloa chinensis*; Chinese sprangletop
LEFSS=*Leptochloa* spp, sprangletop
PANDI=*Panicum dichotomiflorum*
PLALA=*Plantago lanceolata* L.; narrow-leaved plantain
SCPJU=*Scirpus juncoide*; Japanese bulrush
SEBEX=*Sesbania exaltata*; Hemp *sesbania*
Ob=observed value (% control)
Ex=expected, calculated value using Colby Analysis (% control)
DAA=days after application
g ai/ha=grams active ingredient per hectare
g ae/ha=grams acid equivalent per hectare

What is claimed is:

1. A synergistic herbicidal mixture comprising a synergistically herbicidally effective amount of (a) fluroxypyr, or an agriculturally acceptable salt or ester thereof, and (b) an acetolactate synthase(ALS) inhibitor herbicide, wherein the ALS inhibitor herbicide is from the imidazolinone class of herbicides.

2. The mixture of claim 1 in which fluroxypyr, or an agriculturally acceptable salt or ester thereof, is the meptyl ester.

3. The mixture of claim 1 in which the ALS inhibitor herbicide is imazamox or imazethapyr.

4. The mixture of claim 1 in which the weight ratio of fluroxypyr (acid equivalent) to the ALS inhibitor herbicide (active ingredient) is between about 1:2 and about 140:1.

5. An herbicidal composition comprising an herbicidally effective amount of the herbicidal mixture of claim 1 and an agriculturally acceptable adjuvant and/or carrier.

6. The mixture of claim 3, wherein the ALS inhibitor herbicide is imazamox and wherein the weight ratio of fluroxypyr (acid equivalent) to imazamox (active ingredient) is in the range of from 2.8:1 to 45.5:1.

7. The mixture of claim 3, wherein the ALS inhibitor herbicide is imazethapyr and wherein the weight ratio of fluroxypyr (acid equivalent) to imazethapyr (active ingredient) is 4.1:1.

8. A method of controlling undesirable vegetation in rice, cereal crops, grain crops, pastures, rangelands, IVM, turf, wheat, barley, oats, rye, sorghum, corn, maize, grasslands, fallowland, or aquatics, which comprises contacting the vegetation or the locus thereof with or applying to the soil or water to prevent the emergence or growth of vegetation an herbicidally effective amount of the herbicidal mixture of claim 1.

9. The method of claim 8, wherein the undesirable vegetation is controlled in rice, cereal crops, grain crops, pastures, rangelands, IVM or turf.

10. The method of claim 9, wherein the undesirable vegetation is controlled in rice.

11. The method of claim 8, wherein the ALS inhibitor herbicide is applied at a rate between about 4 g ai/ha and about 100 g ai/ha and fluroxypyr is applied at a rate between about 50 g ae/ha and about 560 g ae/ha.

12. The method of claim 8, wherein the herbicidal mixture is applied postemergence.

13. The method of claim 8, wherein the ALS inhibitor herbicide is imazamox.

14. The method of claim 13, wherein the undesirable vegetation is barnyardgrass, broadleaf signalgrass, or yellow nutsedge.

15. The method of claim 13, wherein the weight ratio of fluroxypyr (acid equivalent) to imazamox (active ingredient) is in the range of from 2.8:1 to 45.5:1.

16. The method of claim 8, wherein the ALS inhibitor herbicide is imazethapyr.

17. The method of claim 16, wherein the undesirable vegetation is sprangletop grass or fall panicum.

18. The method of claim 16, wherein the weight ratio of fluroxypyr (acid equivalent) to imazethapyr (active ingredient) is 4.1:1.

19. The method of claim 8, wherein the components of the herbicidal mixture are applied either separately or as part of a multipart herbicidal system.

* * * * *